United States Patent [19]
Senn et al.

[11] Patent Number: 5,889,882
[45] Date of Patent: *Mar. 30, 1999

[54] DETECTION OF SKIN-LINE TRANSITION IN DIGITAL MEDICAL IMAGING

[75] Inventors: Robert Allen Senn, Rochester; Lori Lynn Barski, Mendon, both of N.Y.

[73] Assignee: Eastman Kodak Company, Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 620,095
[22] Filed: Mar. 21, 1996
[51] Int. Cl.$^6$ ..................................................... G06K 9/34
[52] U.S. Cl. ........................... 382/132; 378/62; 382/199; 706/924
[58] Field of Search ................................. 378/37, 62, 98, 378/901; 382/132, 199, 266, 128, 130, 131; 395/924; 128/915, 916; 600/420, 425, 437, 443, 447, 473, 476; 706/924

[56] References Cited

U.S. PATENT DOCUMENTS

| | | | |
|---|---|---|---|
| 5,268,967 | 12/1993 | Jang et al. | 382/132 |
| 5,345,513 | 9/1994 | Takeda et al. | 382/132 |
| 5,452,367 | 9/1995 | Bick et al. | 382/128 |
| 5,572,565 | 11/1996 | Abdel-Mottaleb | 382/132 |
| 5,633,511 | 5/1997 | Lee et al. | 382/132 |

*Primary Examiner*—Scott Rogers
*Assistant Examiner*—Marc Bobys
*Attorney, Agent, or Firm*—William F. Noval

[57] ABSTRACT

A method of determining the skin-line in a digital medical image comprising the steps of:
  providing a digital medical image including a matrix of lines and columns of pixels;
  determining the minimum gray level of the background pixels using a background detection routine;
  selecting all or at least a representative sample of said lines and/or columns of said image, and for each selected line or column;
  smoothing the line to minimize the effect of noise on the delineation of pixel gray level transitions;
  identifying significant transitions from segments of monotonically decreasing gray level values that span a minimum gray level range and start near or above said minimum background gray level;
  computing a set of features for each identified significant transition; and
  based on the set of features computed for each of the identified significant transitions, classifying the transition as either a skin-line transition or as a non-skin-line transition.

13 Claims, 3 Drawing Sheets

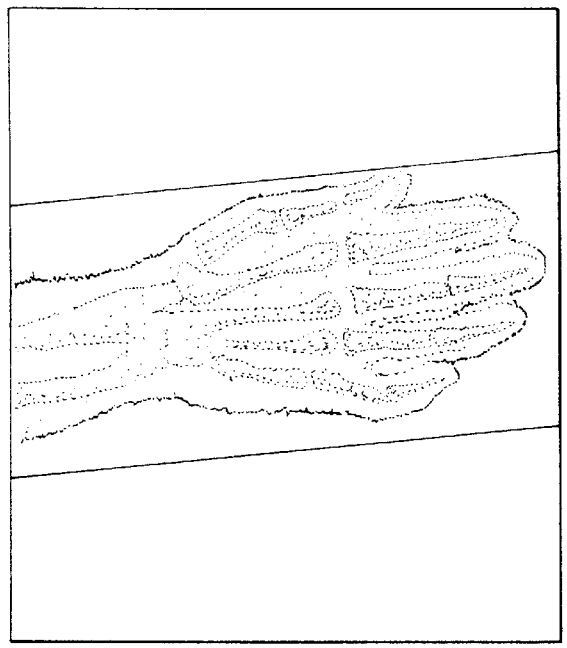
FIG. 4
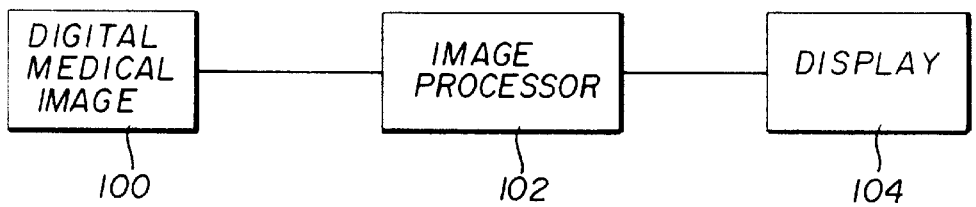
FIG. 5
| FEATURE | DESCRIPTION |
|---|---|
| 0 | TRANSITION LENGTH |
| 1 | TRANSITION RANGE |
| 2 | TRANSITION BACKGROUND DEVIATION |
| 3 | TRANSITION MAXIMUM SLOPE |
| 4 | COEF. OF $x^2$ OF EQ.(1), i.e. A |
| 5 | COEF. OF $x*y$ OF EQ.(1), i.e. B |
| 6 | COEF. OF $y^2$ OF EQ.(1), i.e. C |
| 7 | COEF. OF $x$ OF EQ.(1), i.e. D |
| 8 | COEF. OF $y$ OF EQ.(1), i.e. E |
| 9 | SUM OF SQUARED ERRORS OF THE MODEL FIT |
FIG. 6

DETECTION OF SKIN-LINE TRANSITION IN DIGITAL MEDICAL IMAGING

FIELD OF THE INVENTION

This invention relates in general to digital medical imaging and relates more particularly to a method for the detection of the skin-line transitions in digital medical imaging. Knowledge of the skin-line location may be beneficial in a variety of medical image processing applications including tone-scaling, image segmentation, and body part detection and identification.

BACKGROUND OF THE INVENTION

The tone-scaling processes used to render a digital medical image for output (hardcopy or softcopy) can often result in the loss of definition of the skin-line. Knowledge of the location (and associated gray levels) of the skin-line would allow the tone-scale process to be done in a manner that preserves the definition of the skin-line. Segmentation of the body part from the background (area of direct exposure) and foreground (unexposed area behind masking) can be problematic at the skin boundary due to the gray levels overlapping those of the foreground which limits the effectiveness of thresholding techniques. On the other hand, techniques that utilize spatial information (e.g., texture measures) have inherent limitations at boundaries due to the finite spatial window of pixels over which the measures are computed. Knowledge of the skin-line may allow improved segmentation or body part detection. Additionally, the shape of the skin-line boundary may be an effective feature for identifying the body part or exam type (e.g., chest vs. hand). It is therefore desirable to provide a method for the detection of the skin-line in digital medical imaging.

U.S. Pat. No. 5,452,367, issued Sep. 19, 1995, inventors Bick et al., discloses a method of skin-line detection including the step of first segmenting the body part from the foreground and background. The segmentation is based on the proximity of a pixel's gray level value to the peak of the global histogram, the gray level range over a 7×7 local window of pixels, and the membership of the pixel to a large connected region. After segmentation, the contour distinguishing the segments is inspected and processed to define the skin-line. This method is disadvantageous in requiring segmentation before skin-line detection.

SUMMARY OF THE INVENTION

According to the present invention, there is provided a solution to these problems. The present invention has the following advantages. In contrast to the method of Bick, the method of the present invention provides for the direct detection of the skin-line without prior segmentation of the image. This can provide for better localization of the skin-line since segmentation methods based on gray level and local area measures can be unreliable at the skin-line boundary. The skin-line determined by the direct detection approach of the present invention can be used to improve such image segmentations. Additionally, the estimate of the gray level values associated with the skin-line, which is required for tone-scale applications, is not biased by the use of gray level thresholding techniques often associated with the segmentation process. In summary, advantages of the present invention include the direct detection of the skin-line without prior segmentation, fast line-by-line processing, and minimal dependence on absolute gray level values.

According to a feature of the present invention there is provided a method of determining the skin-line in a digital medical image comprising the steps of:

providing a digital medical image including a matrix of lines and columns of pixels;

determining the minimum gray level of the background pixels using a background detection routine;

selecting all or at least a representative sample of said lines and/or columns of said image, and for each selected line or column;

smoothing said line to minimize the effect of noise on the delineation of pixel gray level transitions;

identifying significant transitions from segments of monotonically decreasing gray level values that span a minimum gray level range and start near or above said minimum background gray level;

computing a set of features for each identified significant transition; and based on the set of features computed for each of said identified significant transitions, classifying said transition as either a skin-line transition or as a non-skin-line transition.

DESCRIPTION OF THE DRAWINGS

FIG. 4 is a depiction of a medical image showing a hand x-ray with skin-line pixels marked in dark gray.

FIG. 5 is a block diagram of apparatus in which the method of the present invention can be used.

FIG. 6 is a table of features computed for each transition.

DESCRIPTION OF THE EMBODIMENTS

Before describing in greater detail the method of the present invention, there will be described apparatus in which the method may be practiced. As shown in FIG. 5, a digital medical image source (100) can include a medical image archive, a medical imaging modality (e.g., US, MRI, CT, PET), a computed radiography reader, an x-ray film digitizer, or the like. The digital medical image from source (100) includes an array of lines and columns of pixels having a gray scale range of a predetermined range of bits or code values (e.g., 8 or 12 bits). The digital medical image from source (100) is processed by image processor (102). Image processor (102) can be a digital computer having well known components such as memory, a central processing unit, input and output devices, etc. Image processor (102) is connected to a display (104) for displaying the processed image. A hard copy output such as a printer may also be provided. In general, the method of the present invention is practiced in image processor (102) using well known computer programming techniques.

Figure 1:
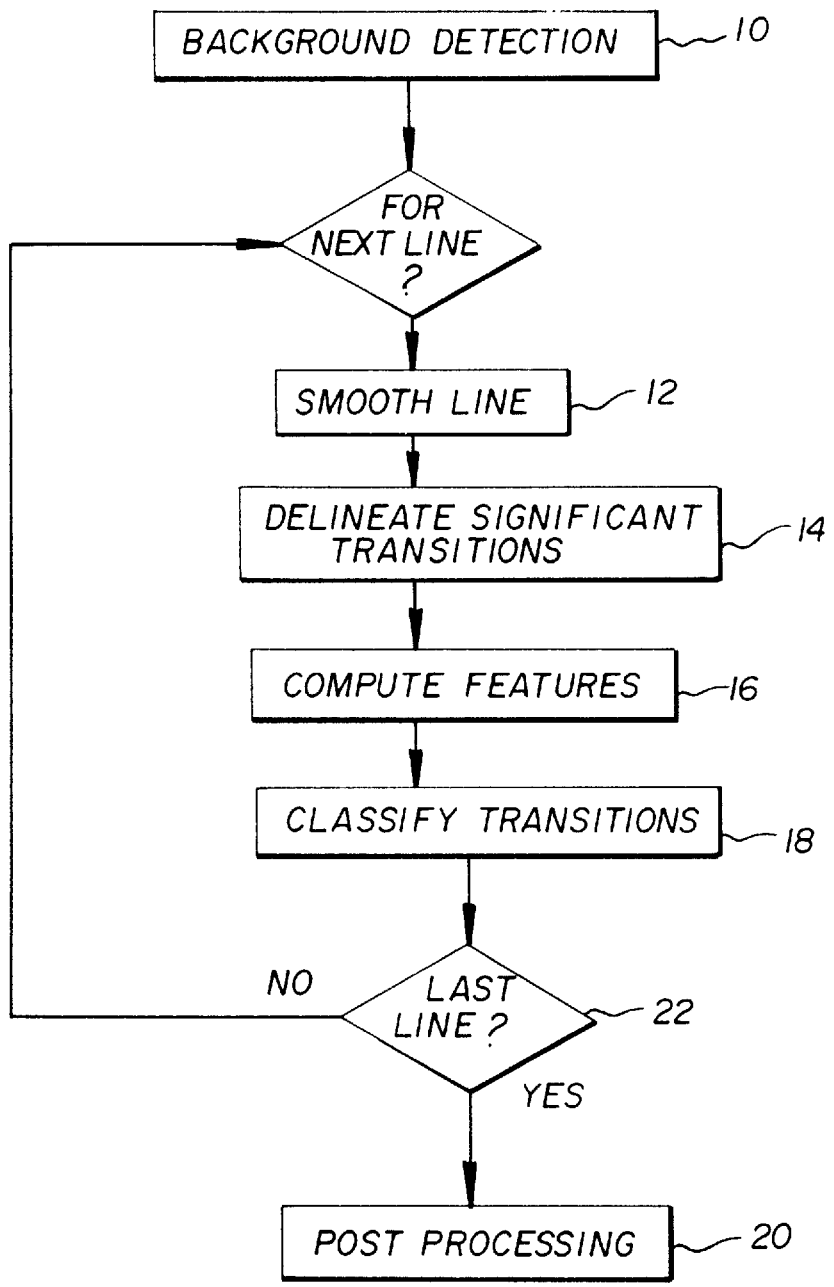
FIG. 1 is a block diagram of the skin-line detection method of the present invention.

In general, the objective of the present invention is to provide a method for identifying the skin-line in digital medical imaging. The preferred form of the output may be a binary mask identifying the skin-line pixels or simply the gray level histogram of the skin-line pixels depending on the application of interest. Referring now to FIG. 1, there is shown a block diagram of the skin-line detection method of the present invention. In the following method although each line and column can be inspected in search of the skin-line, in many applications it may be sufficient to sample the lines and columns of the image.

First, the minimum gray level value of the background (direct exposure) area is estimated (block 10). Then, the line or column being inspected is smoothed to minimize the effect of noise on the delineation of the transitions (block 12). Segments of monotonically decreasing gray level values that span a minimum gray level range, and start near or above the minimum background gray level are identified as significant transitions (block 14). A set of features are computed for each significant transition based on fitting a quadratic model to its line profile (block 16). A classifier then uses the feature vector associated with each transition to label it as a skin-line transition or non-skin-line transition (block 18).

How the skin-line location is reported may be application dependent. A conservative approach with potential application to the tone scale problem is to label the first pixel of the transition as being the skin-line (see FIG. 3). For applications where consistency of the spatial location of the skin line is more important, the point where the transition first reached a given minimum gradient might be used. Depending upon the application, post processing may be desirable (box 20), after the last line (or column) has been processed (decision element 22).

Following is a more detailed description of the major components of the skin-line detection method of the present invention as described above with respect to FIG. 1.

Background Detention

Since the method of the present invention assumes that the skin-line transition must start from the local background gray level (in fact its the skinbackground transition we are looking for) a background detection routine is first employed to find all of the pixels associated with the background, i.e., the area of the image that receives direct exposure. The method of background detection preferably used is that described in greater detail in copending U.S. application Ser. No. 08/620,074, entitled Determination of Direct X-Ray Exposure Regions in Computed Radiography, inventors Barski and Senn. The minimum gray level of the background pixels is determined and stored.

Line Smoothing

Smoothing each line or column before attempting to identify the transitions prevents transitions from being broken up due to the presence of noise in the image data. The exact form of the smoothing is not critical. For simplicity, preferably there is utilized a 1-dimensional convolution with a Gaussian kernel of width 1 pixel at the 1 sigma point truncated to zero for all distances greater than four pixels from the center. This process is described for example in W. K. Pratt, *Digital Image Processing*, 2nd Ed., pp. 169–191, Wiley, 1991.

Transition Delineating

Figure 2:
FIG. 2 is a depiction of a medical image showing a foot x-ray.
Figure 3:
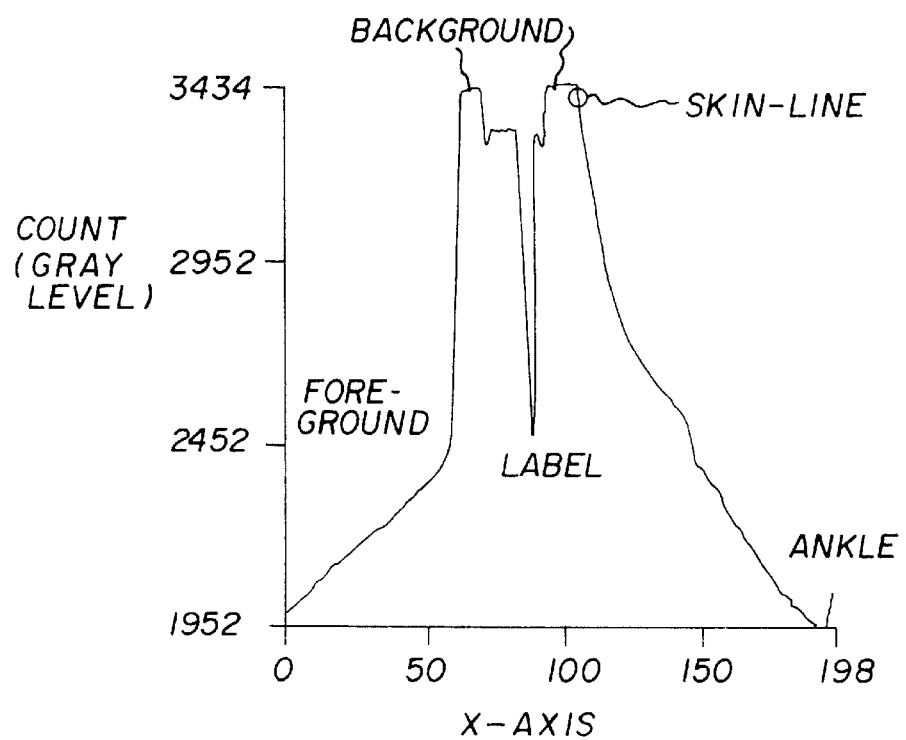
FIG. 3 is a graph of a gray level count vs. x-axis of a line through the label "L" in FIG. 2.

FIGS. 2 and 3 show a foot x-ray image and the profile of a line through the label "L" and the transitions of interest. The smoothed line profile is inspected from both directions for segments that start with gray levels that are not more than some small threshold below the minimum background gray level (as determined above) and have monotonically decreasing gray level values. Not restricting the start of the transition to values greater than the minimum gray level associated with the background allows for some error in the background detection routine. If the range of the gray level transition (monotonically decreasing line segment) exceeds a predefined threshold, the transition is labeled as significant for further consideration as a potential skin-line transition. This eliminates a number of transitions associated with labels, tubes, and other hardware clutter in the scene as well as those associated with the normal image structure of the interior of the body part.

Feature Extraction

A set of 10 features are computed which will be passed to the classifier to distinguish the skin-line transition from the other transitions. Table 1 shown in FIG. 6 lists the features used. The first four [0–3] are computed directly from the transition profile. These include the transition length (in pixels), the transition range (in gray level counts), the deviation of the start of the transition from the background minima (in gray level counts), and maximum slope of the transition as measured across any three pixels. The remaining six features are derived from the least mean square (LMS) error fit of a general quadratic to the transition in question. The quadratic model used is of the form $$A^*x^2 + B^*xy + C^*y^2 + D^*x + E^*y + 1 = 0 \tag{1}$$

where x is the pixel location (in the transition) and y is the gray level value calibrated to be proportional to the logarithm of the exposure. The five parameters associated with the LMS fit (A–E of eq. 1) and the sum of the squared errors between the profile defined by the model and that of the transition in question are used as the last six features. The process of LMS error fitting of a polynomial to a set of data points (in this case defined by the 1-dimensional profile of the transition) is presented in detail in W. H. Press, et al., *Numerical Recipes in C: The Art of Scientific Computing*, Second edition, pp. 656–680, Cambridge University Press, 1992.

Classification

The objective of the classification step is to separate the significant transitions based on the extracted features associated with each transition. A discriminant function (Gaussian maximum likelihood classifier) is used to classify each transition as being either skin-line (i.e., skin-background), foreground-background, body interior, or hardware-background. The decision criteria for a feature vector v associated with a given transition can be stated as $$MIN[\tfrac{1}{2}(v-\mu_i)^T \Sigma_i^{-1}(v-\mu_i) + \tfrac{1}{2}\ln|\Sigma_i| - \ln(P_i)] \tag{2}$$

over all classes i. T=transpose, $|\uparrow|$=determinant, ln=natural log. The mean vector $\mu_i$, covariance matrix $\Sigma_i$, and the prior class probability $P_i$ must be estimated for each class i using available sample transitions of known classification. Details of the design process for a statistical classifier can be found in K. Fukunaga, *Introduction to Statistical Pattern Recognition*, 2nd ed., pp. 169–171, Academic Press, 1990.

FIG. 4 shows an example of the classifier output with skin-line pixels of an x-ray image of a hand shown in dark gray. The preferred implementation of the classifier may depend on the amount of training data (sample images) available for training. The method of this invention is not limited to the use of a statistical parametrics classifiers and might benefit from the use of a non-parametric classifier (e.g., K-NN or neural network), if sufficient training samples are available.

Post Processing

Additional post processing may be desired based on the application of interest. Due to the nature of the problem, the statistical classifier will result in some false positive skin-line detections. In the case of the tone scale application, where the range of the gray level values associated with the skin-line is of primary interest, the histogram of the gray level values can be computed. Outliers or pixels associated with bins at the extremes of the histogram which contain fewer than some threshold level (number of pixels) could be removed. in the case where the spatial location of the skin line is of primary interest (e.g., image segmentation, body part identification), some spatial smoothing or interpolation may be warranted.

The invention has been described in detail with respect to preferred embodiments thereof, but it will be understood that variations and modification can be effected within the spirit and scope of the invention.

What is claimed is:

1. A method of determining the skin-line in a digital medical image comprising the steps of:

providing a digital medical image including a matrix of lines and columns of pixels; and before processing said digital medical image using any histogram processing, or any segmenting processing, processing said digital medical image as follows, determining the minimum gray level of the background pixels using a background detection routine;

selecting all or at least a representative sample of said lines and/or columns of said image, and for each selected line or column;

smoothing said selected line or column to minimize the effect of noise on the delineation of pixel gray level transitions;

identifying significant transitions from segments of monotonically decreasing gray level values that span a minimum gray level range and start near or above said minimum background gray level;

computing a set of features for each identified significant transition; and based on the set of features computed for each of said identified significant transitions, classifying said transition as either a skin-line transition or as a non-skin-line transition.

2. The method of claim 1 wherein said smoothing step utilizes a 1-dimensional convolution with a Gaussian kernel of width 1 pixel at the 1 sigma point truncated to zero at all distances greater than four pixels from the center.

3. The method of claim 1 wherein said computing step computes a set of features which include a first subset of features which are computed directly from the said transition profile and which includes a second subset of features which are derived from the least mean square error fit of a general quadratic to the transition.

4. The method of claim 3 wherein said first subset of features which are computed directly from said transition profile include the transition length in pixels, the transition range in gray level counts, the deviation of the transition from the background minima in gray level counts, and the maximum slope of the transition as measured across any three pixels.

5. The method of claim 3 wherein said second subset of features are derived from the least mean square error fit of the quadratic equation $$A*x^2 + B*xy + C*y^2 + D*x + E*y + 1 = 0$$

where x is the pixel location in the transition, y is the gray level value calibrated to be proportional to the logarithm of exposure of the medical image and A, B, C, D, and E are coefficients and said second subset of features include the coefficients A, B, C, D, E and the sum of the squared errors of the model fit.

6. The method of claim 1 wherein said classifying step is carried out using a statistical classifier.

7. The method of claim 1 wherein said classifying step is carried out using a discriminant function to classify each transition as being either a skin-line (i.e., skin-background), foreground-background, body interior, or hardware-background.

8. The method of claim 7 wherein said classifying step is carried out using the Gaussian maximum likelihood classifier discriminant function, wherein the decision criteria for a feature vector v associated with a given transition can be stated as $$MIN[\tfrac{1}{2}(V-\mu_i)^T \Sigma_i^{-1}(v-\mu_i) + \tfrac{1}{2} \ln|\Sigma_i| - \ln(P_i)]$$

over all classes i, where the mean vector $\mu_i$, covariance matrix $\Sigma_i$, and the a prior class probability $P_i$ must be estimated for each class i using available sample transitions of known classifications.

9. The method of claim 1 including the further step of minimizing false positive skin-line transitions in a tone scale application by computing the histogram of the gray level values and eliminating pixels associated with bins at the extremes of the histogram which contain fewer than a preselected threshold number of pixels.

10. The method of claim 1 including the further step of minimizing false positive skin-line transitions where the spatial location of the skin-line is of primary interest by spatial smoothing or interpolation.

11. The method of claim 1 wherein said classified skin-line transitions are represented as a binary mask identifying the skin-line pixels.

12. The method of claim 1 wherein said classified skin-line transitions are represented by a gray-level histogram of the skin-line pixels.

13. A computer program product comprising a computer readable storage medium having a computer program stored thereon for performing the method of claim 1.

* * * * *